United States Patent
Hancock

(10) Patent No.: US 9,629,553 B2
(45) Date of Patent: Apr. 25, 2017

(54) SEAM ELIMINATION AND MOTION COMPENSATION IN IMAGING DATA

(71) Applicant: VOLCANO CORPORATION, San Diego, CA (US)

(72) Inventor: Andrew Hancock, Sacramento, CA (US)

(73) Assignee: Volcano Corporation, San Diego, CA (US)

( * ) Notice: Subject to any disclaimer, the term of this patent is extended or adjusted under 35 U.S.C. 154(b) by 0 days.

(21) Appl. No.: 14/964,315

(22) Filed: Dec. 9, 2015

(65) Prior Publication Data
US 2016/0180519 A1    Jun. 23, 2016

Related U.S. Application Data

(60) Provisional application No. 62/094,303, filed on Dec. 19, 2014.

(51) Int. Cl.
*A61B 5/00* (2006.01)
*A61B 8/14* (2006.01)

(52) U.S. Cl.
CPC .......... *A61B 5/0066* (2013.01); *A61B 5/0084* (2013.01); *A61B 5/7207* (2013.01); *A61B 8/14* (2013.01); *A61B 5/0037* (2013.01)

(58) Field of Classification Search
CPC ....... A61B 5/0066; A61B 8/14; A61B 5/0037; A61B 5/0084; A61B 5/7207; G06T 2207/10101; G06T 2207/10132; G06T 5/002; G06T 7/0012

USPC ......................................................... 382/128
See application file for complete search history.

(56) References Cited

U.S. PATENT DOCUMENTS

| | | | | |
|---|---|---|---|---|
| 6,148,095 A * | 11/2000 | Prause | .................... | G06T 17/00 128/916 |
| 8,727,990 B2 * | 5/2014 | Kim | .................... | G01S 15/8995 600/443 |
| 9,480,403 B2 * | 11/2016 | Perrey | .................. | A61B 5/0044 |
| 2008/0287795 A1 * | 11/2008 | Klingensmith | .... | A61B 5/02007 600/443 |
| 2012/0059253 A1 * | 3/2012 | Wang | ....................... | A61B 6/00 600/427 |
| 2014/0039308 A1 * | 2/2014 | Blanz | ..................... | A61B 8/52 600/425 |

* cited by examiner

*Primary Examiner* — Tom Y Lu

(57) ABSTRACT

Imaging devices, systems, and methods are provided. Some embodiments of the present disclosure are particularly directed to removing artifacts caused by longitudinal motion of a sensor during imaging. In some embodiments, a medical sensing system includes a de-seaming engine operable to receive a first signal at a first point and second signal at a second point. The first and second points are offset from the pixel in the longitudinal direction. The de-seaming engine corrects for movement in the longitudinal direction by determining a weighted average of the first signal and the second signal. The engine determines a first probability based on the first signal and the weighted average and determines a second probability based on the second signal and the weighted average. The engine selects one of the first and second signal intensities as an intensity of the pixel based on the first and second probabilities.

20 Claims, 8 Drawing Sheets

SEAM ELIMINATION AND MOTION COMPENSATION IN IMAGING DATA

CROSS REFERENCE TO RELATED APPLICATIONS

The present application claims priority to and the benefit of the U.S. Provisional Patent Application No. 62/094,303, filed Dec. 19, 2014, which is hereby incorporated by reference in its entirety.

TECHNICAL FIELD

The present disclosure relates generally to imaging and, in particular, to correcting for longitudinal movement of an imaging device during data acquisition. In various embodiments, the medical sensing system includes an intravascular portion having an elongate member with one or more sensors such as ultrasound transducers and/or optical coherence tomography sensors oriented to collect data radially as the elongate member is drawn longitudinally through a vessel. The medical sensing system assembles the radial data into cross-sectional slices of the vessel. Due to the longitudinal motion, the radial data is actually a helical representation of the vessel and according, the medical sensing system flattens the helical data to produce a cross-sectional view. The system is suitable for use in a variety of applications including intravascular ultrasound. For example, some embodiments of the present disclosure provide an IVUS medical sensing system particularly suited to imaging a human blood vessel.

BACKGROUND

Innovations in diagnosing and verifying the level of success of treatment of disease have migrated from external imaging processes to internal diagnostic processes. In particular, diagnostic equipment and processes have been developed for diagnosing vasculature blockages and other vasculature disease by means of ultra-miniature sensors placed upon the distal end of a flexible elongate member such as a catheter, or a guide wire used for catheterization procedures. For example, known medical sensing techniques include angiography, intravascular ultrasound (IVUS), forward looking IVUS (FL-IVUS), fractional flow reserve (FFR) determination, a coronary flow reserve (CFR) determination, optical coherence tomography (OCT), transesophageal echocardiography, and image-guided therapy.

For example, intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. There are two general types of IVUS devices in use today: rotational and solid-state (also known as synthetic aperture phased array). For a typical rotational IVUS device, a single ultrasound transducer element is located at the tip of a flexible driveshaft that spins inside a plastic sheath inserted into the vessel of interest. In side-looking rotational devices, the transducer element is oriented such that the ultrasound beam propagates generally perpendicular to the longitudinal axis of the device. In forward-looking rotational devices, the transducer element is pitched towards the distal tip so that the ultrasound beam propagates more towards the tip (in some devices, being emitted parallel to the longitudinal centerline). The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS medical sensing system assembles a two dimensional display of the tissue, vessel, heart structure, etc. from a sequence of pulse/acquisition cycles occurring during a single revolution of the transducer. In order to image a length of a vessel, the transducer element is drawn through the vessel as it spins.

In contrast, solid-state IVUS devices utilize a scanner assembly that includes an array of ultrasound transducers connected to a set of transducer controllers. In side-looking and some forward-looking IVUS devices, the transducers are distributed around the circumference of the device. In other forward-looking IVUS devices, the transducers are a linear array arranged at the distal tip and pitched so that the ultrasound beam propagates closer to parallel with the longitudinal centerline. The transducer controllers select transducer sets for transmitting an ultrasound pulse and for receiving the echo signal. By stepping through a sequence of transmit-receive sets, the solid-state IVUS system can synthesize the effect of a mechanically scanned transducer element but without moving parts. Since there is no rotating mechanical element, the transducer array can be placed in direct contact with the blood and vessel tissue with minimal risk of vessel trauma. Furthermore, because there is no rotating element, the interface is simplified. The solid-state scanner can be wired directly to the medical sensing system with a simple electrical cable and a standard detachable electrical connector. While the transducers of the scanner assembly do not spin, operation is similar to that of a rotational system in that, in order to image a length of a vessel, the scanner assembly is drawn through the vessel while stepping through the transmit-receive sets to produce a series of radial scans.

Rotational and solid-state state IVUS are merely some examples of imaging modalities that sample a narrow region of the environment and assemble a two- or three-dimensional image from the results. Other examples include optical coherence tomography (OCT). One of the key challenges in this type of imaging is inferring information in areas of the environment that are not directly imaged. In the preceding examples where a narrow beam rotates around the axis, the radial data is only coplanar if there is no movement during a rotation. In more common applications where the scanning element is drawn through the vessel during imaging, each radially imaged region will have a different longitudinal orientation. In other words, the scanner assembly images a helical region rather than a set of flat circular regions. If the helical data is simply flattened, a discontinuity or seam may occur between the first and last radial scans of the image. In addition to being visually unappealing, the seam also indicates that the scanning data is being incorrectly displayed. For example, improper flattening may hide the curvature of the vessel. Effects due to improper flattening become more pronounced as the longitudinal motion becomes greater relative to the rotational speed. For example, OCT may have a much higher relative pullback speed than IVUS, resulting in more longitudinal distortion and may experience an even greater benefit from proper correction.

Accordingly, a more accurate technique for reconstructing a planar cross-section from non-planar data would produce a more accurate image that is closer to what a clinician would expect and may thus improve diagnostic accuracy. As an additional benefit, it may reduce or eliminate distortions and discontinuities (e.g., seams). For these reasons and others, the need exists for improved systems and techniques that account for longitudinal motion of a scanning element and for compensating when interpolating data.

SUMMARY

Embodiments of the present disclosure provide an imaging component that assembles a cross-sectional representation from a helical set of imaging data and removes artifacts caused by conventional flattening processes. The imaging component may be used in applications such as an intravascular ultrasound medical sensing system.

In some embodiments, a medical sensing system is provided. The system comprises a de-seaming engine operable to receive a first signal at a first point and a second signal at a second point. The first point and the second point may have similar relative positions while being in different frames. In other words, the first and second points may have the same radial and azimuthal orientation but occupy different positions longitudinally. The de-seaming engine determines an intensity at a location between the first and second points using the first signal and the second signal. To achieve this, the de-seaming engine includes an averaging element operable to determine a weighted average of the first signal and the second signal. The weighted average is used to determine an interpolated signal value at the location based on the signal values measured at the first and second points. Accordingly, the de-seaming engine also includes a first comparator operable to determine a first probability based on the first signal and the weighted average and a second comparator operable to determine a second probability based on the second signal and the weighted average. The first and second probabilities are provided to a third comparator of the de-seaming engine, which is operable to select one of the first and second signal intensities as an intensity at the location based on the first and second probabilities and to provide the selected intensity as a pixel intensity for forming an image.

In some embodiments, a method is provided. The method includes receiving a first signal value associated with a first point located a first longitudinal distance from a pixel and a second signal value associated with a second point located a second longitudinal distance from the pixel. A first probability associated with the first point is determined based on the first longitudinal distance, and a second probability associated with the second point is determined based on the second longitudinal distance. A signal value for the pixel is selected based on the first probability and the second probability, and the selected signal value for the pixel is provided for forming an image. In some such embodiments the method also includes determining a first weighting factor for the first point based on the first longitudinal distance and determining a second weighting factor for the second point based on the second longitudinal distance. A weighted average is determined based on the first signal value, the first weighting factor, the second signal value, and the second weighting factor. The determining of the first probability includes comparing the first signal value to the weighted average, and the determining of the second probability includes comparing the second signal value to the weighted average.

In further embodiments, a method of diagnostic imaging is provided. The method includes identifying a pixel located between a first point and a second point in a longitudinal direction. A first imaging signal for the first point and a second imaging signal for the second point are received, and a weighted average of the first imaging signal and the second imaging signal is determined. The first signal is compared to the weighted average to determine a first probability, and the second signal is compared to the weighted average to determine a second probability. A value for the pixel is selected based on the first probability and the second probability. The selected value is provided for use in forming a diagnostic image. In some such embodiments, the method also includes determining a first weighting factor for the first imaging signal based on a longitudinal distance between the first point and the pixel and determining a second weighting factor for the second imaging signal based on a longitudinal distance between the second point and the pixel. The determining of the weighted average includes applying the first weighting factor to the first imaging signal and applying the second weighting factor to the second imaging signal. In some such embodiments, the first weighting factor is determined based on a count of radial measurements between the first point and the pixel, and the second weighting factor is determined based on a count of radial measurements between the second point and the pixel.

In this way, the techniques of the present disclosure interpolate a value at the pixel using the adjacent first and second points by accounting for longitudinal movement of a scanner element. By so doing, the technique removes discontinuities (e.g., seams) and/or other distortions from the resulting image. In addition to being more visually appealing, the de-seamed image provides for more accurate measurements of the surrounding tissue. In many embodiments, by selecting from the first and second signal intensities rather than averaging the intensities, the resulting image is also free of feature doubling, the tendency of a single feature to be present at more than one location in the image. Compared to other techniques, a medical sensing system is able to perform this interpolation without loss of resolution, blurring, or unintended filtering of features. The de-seaming technique may be performed on a variety of sensing data types including ultrasound echo data and optical coherence tomography data and does not require prior conversion of the data to any particular representation (e.g., baseband or time-domain). Of course, these advantages are merely exemplary, and no single advantage is characteristic of or required for any particular embodiment.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1A:
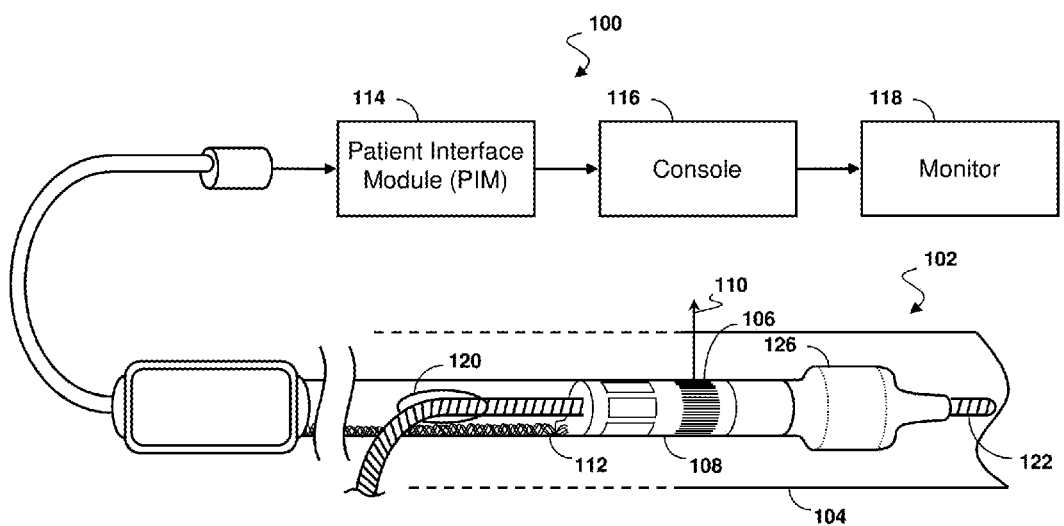
FIGS. 1A and 1B are diagrammatic schematic views of a medical sensing system according to some embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the intravascular sensing system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1A is a diagrammatic schematic view of a medical sensing system 100 according to some embodiments of the present disclosure. The medical sensing system 100 includes an elongate member 102 (such as a catheter, guide wire, or guide catheter) of the medical sensing system 100. As used herein, "elongate member" or "flexible elongate member" includes at least any thin, long, flexible structure that can be inserted into the vasculature of a patient. While the illustrated embodiments of the "elongate members" of the present disclosure have a cylindrical profile with a circular cross-sectional profile that defines an outer diameter of the flexible elongate member, in other instances, all or a portion of the flexible elongate members may have other geometric cross-sectional profiles (e.g., oval, rectangular, square, elliptical, etc.) or non-geometric cross-sectional profiles. Flexible elongate members 102 include, for example, guide wires, catheters, and guide catheters. In that regard, a catheter may or may not include a lumen extending along its length for receiving and/or guiding other instruments. If the catheter includes a lumen, the lumen may be centered or offset with respect to the cross-sectional profile of the device.

The medical sensing system 100 may be utilized in a variety of applications and can be used to assess vessels and structures within a living body. To do so, the elongate member 102 is advanced into a vessel 104. Vessel 104 represents fluid filled or surrounded structures, both natural and man-made, within a living body that may be imaged and can include for example, but without limitation, structures such as: organs including the liver, heart, kidneys, as well as valves within the blood or other systems of the body. In addition to imaging natural structures, the images may also include man-made structures such as, but without limitation, heart valves, stents, shunts, filters and other devices positioned within the body. The elongate member 102 includes sensors 106 disposed along the length of the member 102 to collect diagnostic data regarding the vessel 104. In various embodiments, the sensors 106 correspond to sensing modalities such as flow, optical flow, IVUS, photoacoustic IVUS, FL-IVUS, pressure, optical pressure, fractional flow reserve (FFR) determination, coronary flow reserve (CFR) determination, OCT, transesophageal echocardiography, image-guided therapy, other suitable modalities, and/or combinations thereof.

In the exemplary embodiment of FIG. 1A, the elongate member 102 includes a solid-state IVUS device, and the sensors 106 include an array of IVUS ultrasound transceivers and associated control circuitry incorporated into a scanner assembly 108. The sensors 106 may be arranged around the circumference of the elongate member 102 and positioned to emit ultrasound energy radially 110 in order to obtain a cross-sectional representation of the vessel 104 and the surrounding anatomy. When the scanner assembly 108 is positioned near the area to be imaged, the control circuitry selects some of the IVUS transceivers to transmit an ultrasound pulse that is reflected by the vessel 104 and the surrounding structures. The control circuitry also selects some transceivers to receive the echo signal. By stepping through sequences of transmit-receive sets, the medical sensing system 100 system can synthesize the effect of a mechanically scanned transducer element without moving parts.

Figure 1B:
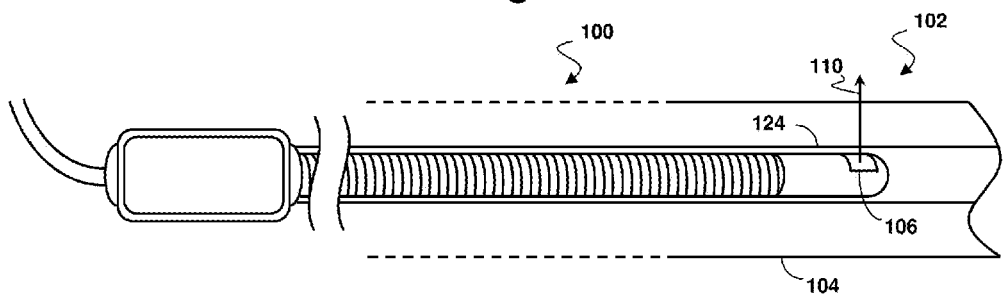

FIG. 1B is a schematic view of a system that includes an alternative elongate member 102 according to some embodiments of the present disclosure. The elongate member 102 of FIG. 1B is typical of a rotational device such as a rotational IVUS ultrasound system and the sensor 106 includes one or more IVUS transducers arranged to emit ultrasound energy in a radial direction 110. In such an embodiment, the sensor(s) 106 may be mechanically rotated around a longitudinal axis of the elongate member 102 to obtain a cross-sectional representation of the vessel 104.

In a further embodiment, sensor 106 includes an OCT transceiver. Other embodiments incorporate other combinations of sensors, and no particular sensor or combination of sensors is required for any particular embodiment.

Data from the sensor(s) 106 is transmitted via a cable 112 to a Patient Interface Module (PIM) 114 and/or a console 114. The PIM 114 is an isolation device as, in various surgical settings, patient safety requirements mandate physical and electrical isolation of the patient. Thus, if complete electrical isolation is required, the PIM 114 and the console 114 may be communicatively coupled by an optical, RF, or other non-conductive link. In less stringent environments, conductive communication links and/or power couplings may extend between the two. Moreover, in some embodiments, the PIM 114 and console 114 are collocated and/or part of the same system, unit, chassis, or module. Together the PIM 114 and console 114 assemble, process, and render the sensor data for display as an image on a monitor 118. For example, in various embodiments, the PIM 114 and/or the console 114 generates control signals to configure the sensor 106, generates signals to activate the sensor 106, performs amplification, filtering, and/or aggregating of sensor data, and formats the sensor data as an image for display. The allocation of these tasks and others between the PIM 114 and the console 114 is merely arbitrary.

In addition to various sensors 106, the elongate member 102 may include a guide wire exit port 120 as shown in FIG. 1A. The guide wire exit port 120 allows a guide wire 122 to be inserted towards the distal end in order to direct the member 102 through a vascular structure (i.e., the vessel) 104. Accordingly, in some instances the elongate member 102 is a rapid-exchange catheter. Additionally or in the alternative, the elongate member 102 is advanced through the vessel 104 inside a guide catheter 124 as shown in FIG. 1B. In an embodiment, the elongate member 102 includes an inflatable balloon portion 126 near the distal tip. The balloon portion 126 is open to a lumen that travels along the length of the IVUS device and ends in an inflation port (not shown). The balloon 126 may be selectively inflated and deflated via the inflation port.

Figure 2:
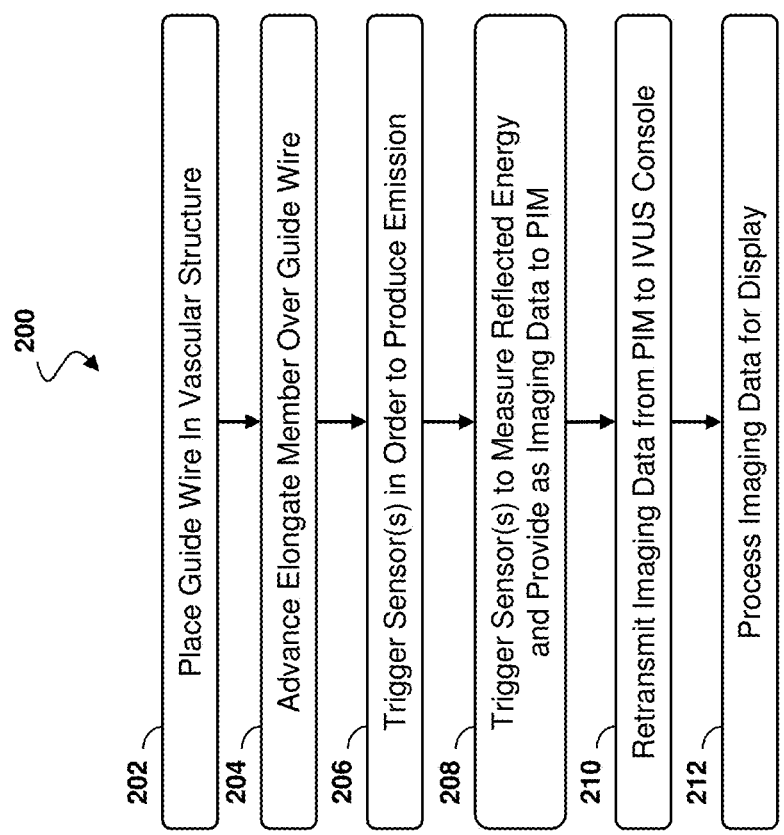
FIG. 2 is a flow diagram of a method of performing a diagnostic procedure using the medical sensing system according to embodiments of the present disclosure.

FIG. 2 is a flow diagram of a method 200 of performing a diagnostic procedure using the medical sensing system 100 according to embodiments of the present disclosure. It is understood that additional steps can be provided before, during, and after the steps of method 200, and that some of the steps described can be replaced or eliminated for other embodiments of the method.

Referring block 202 of FIG. 2 and referring still to FIGS. 1A and 1B, in an illustrative example of a typical environment and application of the system, a surgeon places a guide wire 122 in the vessel 104. The guide wire 122 is threaded through at least a portion of the distal end of the elongate member 102 before, during, or after placement of the guide wire 122. Referring to block 204 of FIG. 2, once the guide wire 122 is in place, the elongate member 102 is advanced over the guide wire. Additionally or in the alternative, a guide catheter 124 is advanced in the vessel 104 in block 202 and the elongate member 102 is advanced within the guide catheter in block 204.

Referring to block 206, once positioned, the sensor 106 is activated. Imaging is described in more detail with reference to FIGS. 3-8, but at a high level, signals sent from the PIM 114 to the sensor 106 via the cable 112 cause the sensor to obtain diagnostic information. In the example of an IVUS application, transducers within the sensor 106 emit a specified ultrasonic waveform. The ultrasonic waveform is reflected by the vessel 104 and the surrounding anatomy. The reflections are received by the transducers and are amplified for transmission via the cable 112. The echo data is placed on the cable 112 and sent to the PIM 114. In the example of an OCT application, an optical emitter within the sensor 106 produces light that is reflected by structures in the surrounding environment. The reflected light is compared to a reference signal by the elongate member 102 or the PIM 114 to obtain intensity and distance measurements.

In these examples and others, the PIM 114 may perform any suitable signal processing or enhancement before retransmitting the sensor data to the console 114 in block 208. Referring to block 210, the console 114 aggregates and assembles the received sensor data to create an image of the vessel 104 for display on the monitor 118. In some exemplary applications, the elongate member 102 is advanced beyond the area of the vessel 104 to be imaged and pulled back as the scanner assembly 108 is operating, thereby exposing and imaging a longitudinal portion of the vessel 104. To ensure a constant velocity, a pullback mechanism is used in some instances. A typical withdraw velocity is 0.5 cm/s. In some embodiments, the member 102 includes an inflatable balloon portion 126. As part of a treatment procedure, the device may be positioned adjacent to a stenosis (narrow segment) or an obstructing plaque within the vessel 104 and inflated in an attempt to widen the restricted area of the vessel 104.

Figure 3:
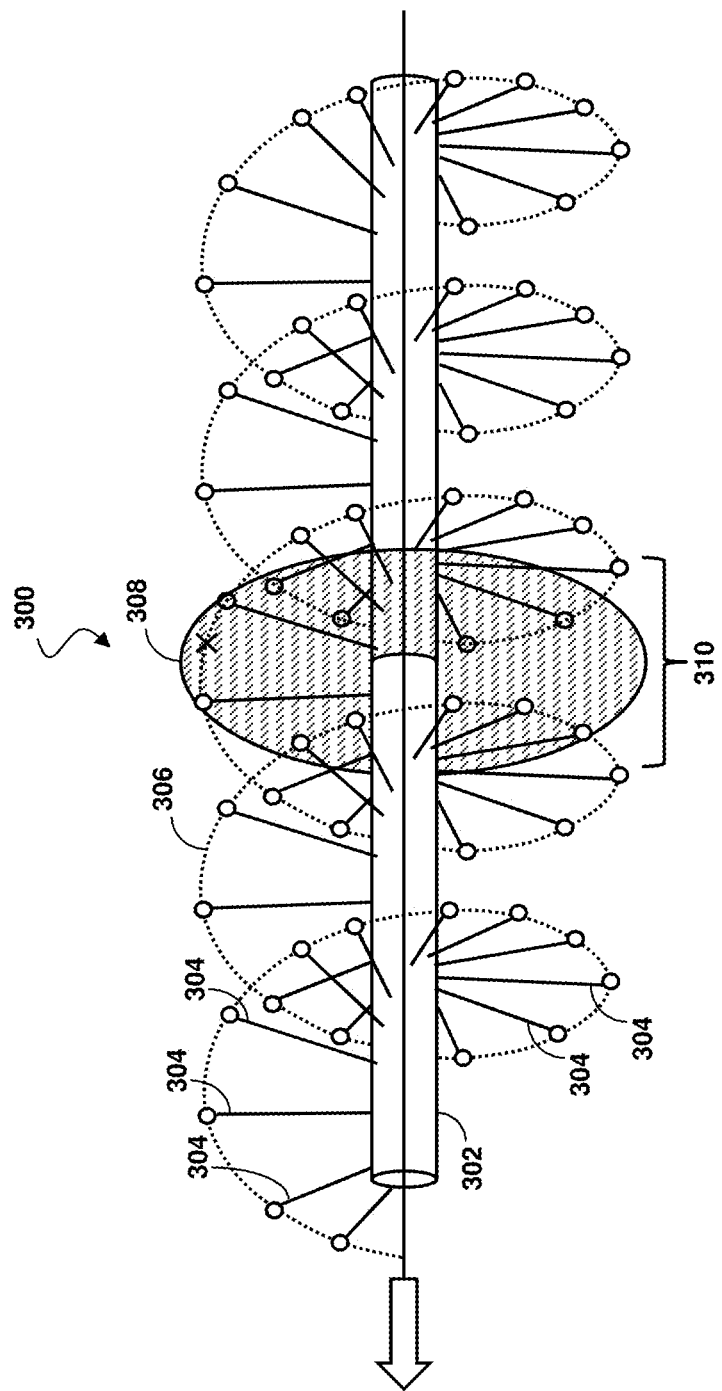
FIG. 3 is a perspective diagram of a path of an elongate member during data acquisition according to embodiments of the present disclosure.
Figure 4:
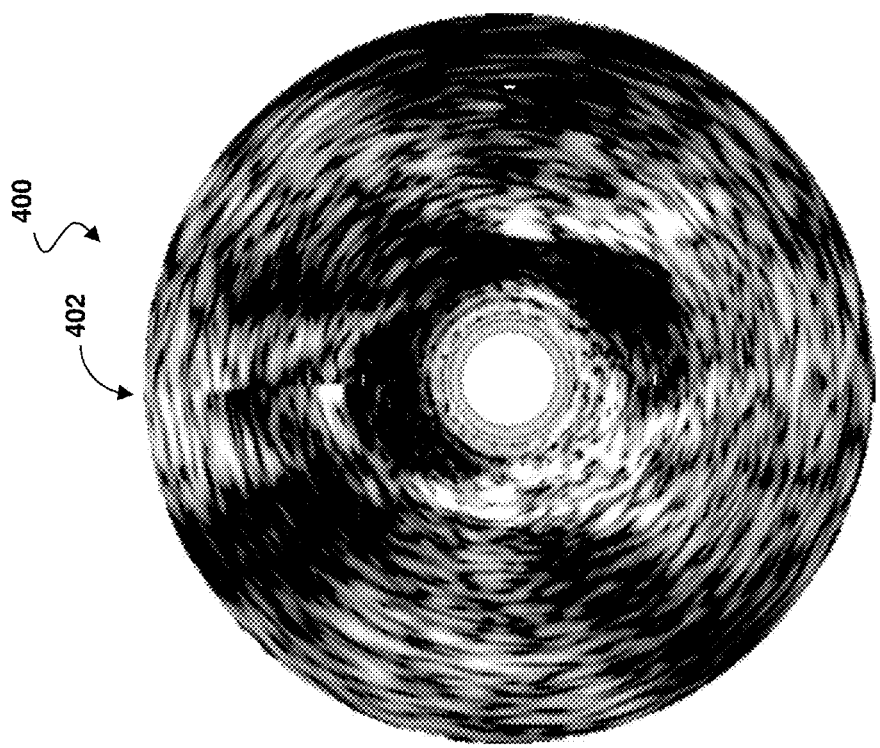
FIG. 4 is a representation of an image produced by a medical sensing system using sensing data acquired by the elongate member according to embodiments of the present disclosure.

Because the sensor(s) 106 collect data as the elongate member 102 is withdrawn longitudinally through the vessel 104, each data point has a longitudinal component in addition to the radial component. The effect of this longitudinal motion on images produced by the medical sensing system 100 is described with reference to FIGS. 3 and 4. FIG. 3 is a perspective diagram of a path 300 of an elongate member 102 during data acquisition according to embodiments of the present disclosure. FIG. 4 is a representation of an image 400 produced by the medical sensing system 100 using sensing data acquired by the elongate member 102 according to embodiments of the present disclosure. FIG. 4 represents an image 400 generated from IVUS echo data although the principles of the present disclosure apply equally to other sensing modalities.

Referring first to FIG. 3, the path 300 of an elongate member 102 is shown. The elongate member 102 travels longitudinally as indicated by cylinder 302, and as it does so, one or more sensors 106 of the elongate member 102 acquire imaging data in a radial direction as indicated by the radial lines 304. Helical line 306 represents the imaged area due to the longitudinal motion and the radial scanning.

In many embodiments, the medical sensing system 100 presents the imaging data on a monitor 118 as a two-dimensional cross section of the surrounding environment. For example, plane 308 of FIG. 3 represents one possible cross-sectional slice. However, when a complete revolution of data is not available in the cross-sectional plane, such as may occur when the elongate member 102 is being pulled back, interpolation is performed using data outside the plane 308. Referring to FIG. 4, in a simple example, data collected from one revolution of the helix (i.e., one frame of data indicated by reference 310 in FIG. 3) centered at the cross-sectional plane is displayed without any further processing. However, this may result in an obvious discontinuity or seam as data from the beginning and end of the revolution are positioned adjacent one another. In the example of FIG. 4, the seam is indicated by reference marker 402. The seam 402 arises because data collected on opposite sides of the seam has different longitudinal positions that are not properly accounted for. The flattening process produces other distortions that are less obvious and may be more troublesome. For example, because the flattened helix is not a true cross-section, it may hide curvature of the vessel 104 and may skew feature measurements.

Figure 8:
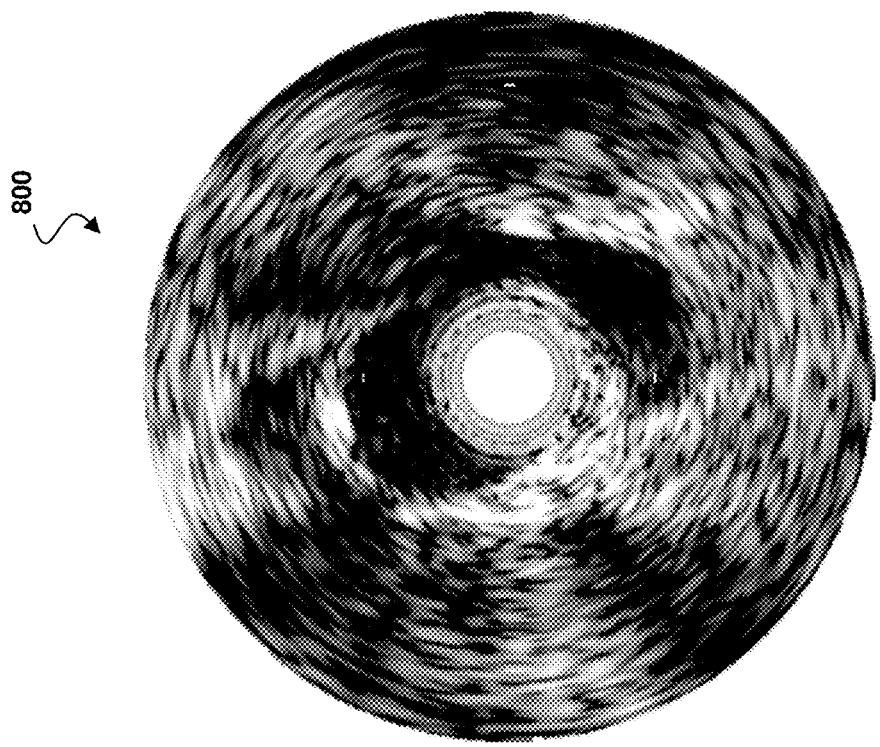
FIG. 8 is a representation of a de-seamed image produced by the medical sensing system according to embodiments of the present disclosure.
Figure 5A:
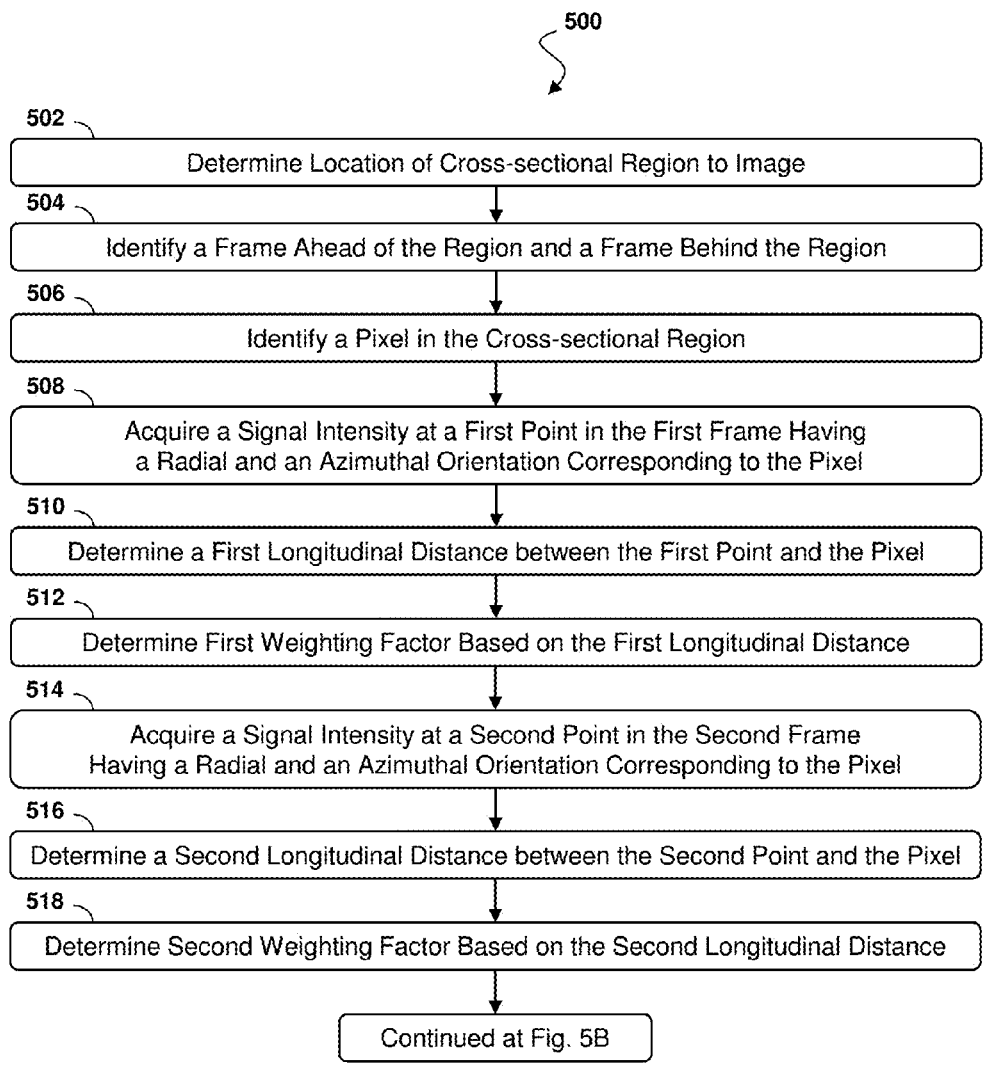
FIGS. 5A and 5B are flow diagrams of a method of motion compensation and seam elimination according to embodiments of the present disclosure.
Figure 5B:
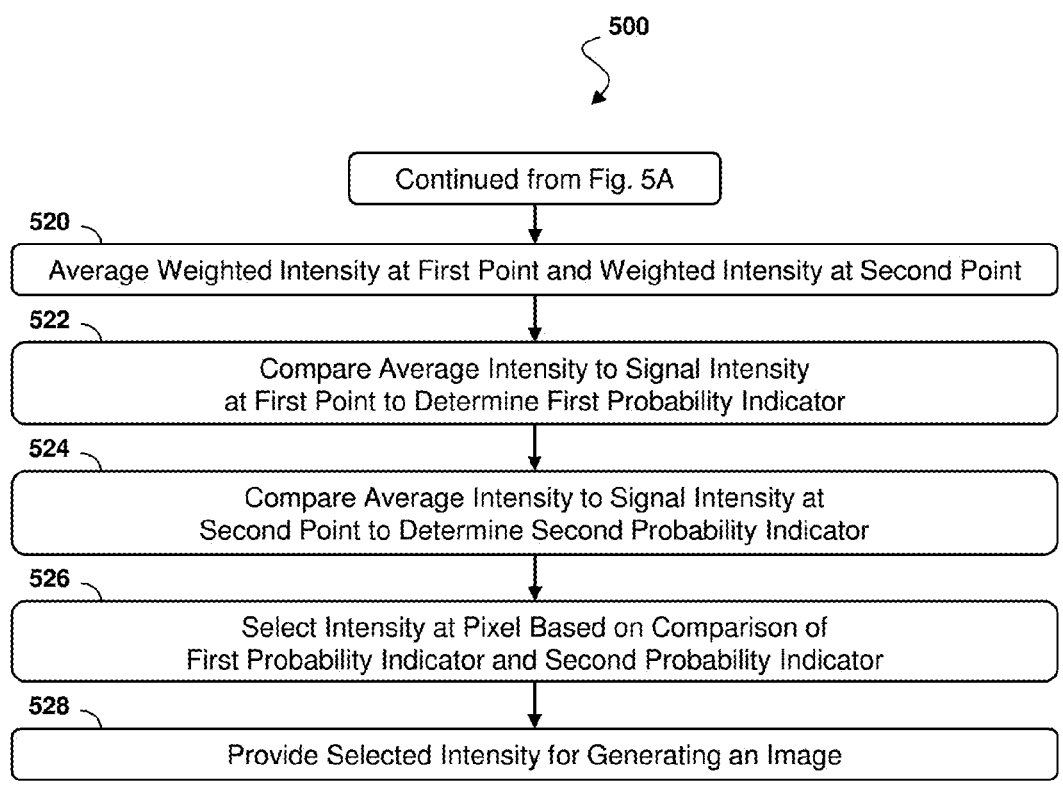
Figure 6:
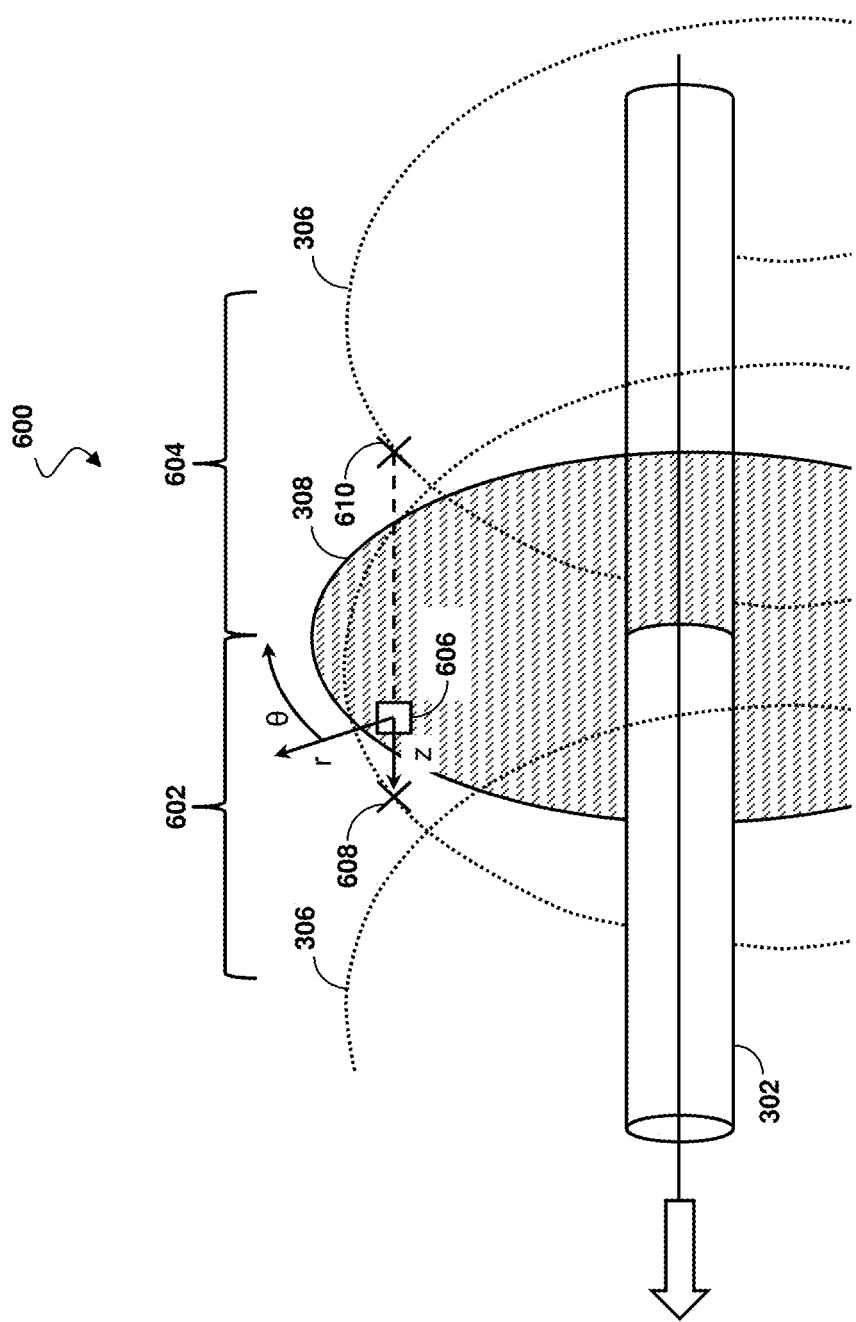
FIG. 6 is a perspective diagram of a path of an elongate member during data acquisition according to embodiments of the present disclosure.
Figure 7:
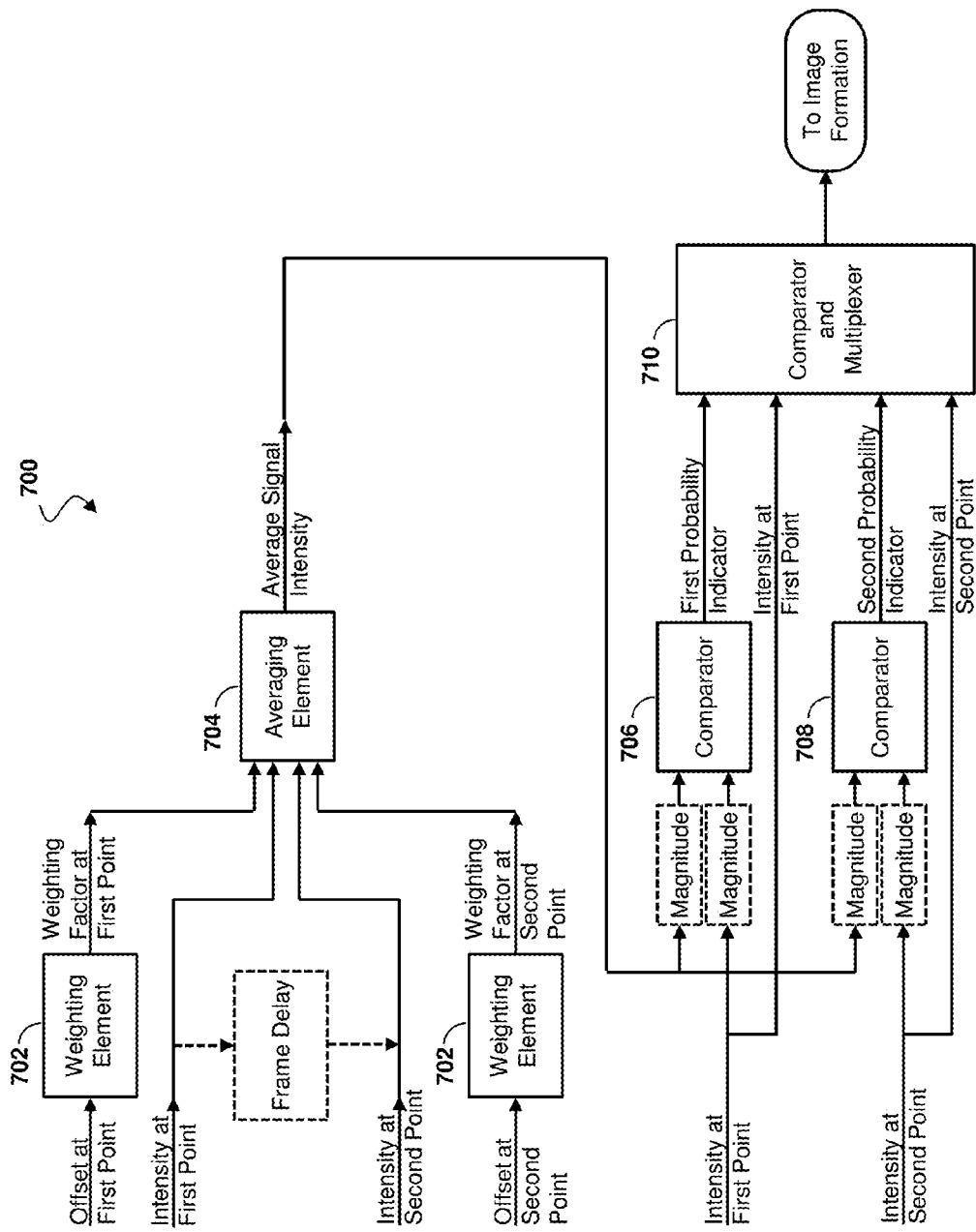
FIG. 7 is a schematic diagram of a de-seaming engine of a medical sensing system according to embodiments of the present disclosure.

Accordingly, a method is provided that corrects for longitudinal motion during data acquisition in order to produce a more accurate cross-sectional image. Embodiments of the method are described with reference to FIGS. 5A-8. FIGS. 5A and 5B are flow diagrams of the method 500 of motion compensation and seam elimination according to embodiments of the present disclosure. It is understood that additional steps can be provided before, during, and after the steps of method 500, and that some of the steps described can be replaced or eliminated for other embodiments of the method. FIG. 6 is a perspective diagram of a path 600 of an elongate member 102 during data acquisition according to embodiments of the present disclosure. FIG. 7 is a schematic diagram of a de-seaming engine 700 of a medical sensing system 100 according to embodiments of the present disclosure. The de-seaming engine 700 may be incorporated into the PIM 114, console 114, and/or any other processing element of the medical sensing system 100 and may operate in conjunction with any other data acquisition, image processing, and/or image analysis elements of the medical sensing system 100. FIG. 8 is a representation of a de-seamed image 800 produced by the medical sensing system 100 according to embodiments of the present disclosure. FIG. 8 represents an image 800 generated from IVUS echo data, although the principles of the present disclosure apply equally to other sensing modalities.

Referring to block 502 of FIG. 5A and referring to FIG. 6, the medical sensing system 100 determines a desired location for a cross-sectional slice in a longitudinal direction. For example, the medical sensing system 100 may produce cross-sectional images at various intervals determined by position and/or time. In some embodiments, the slice/image location need not correspond to a radial beam, and such a medical sensing system 100 supports cross-sectional slices located between the radial beams. In the embodiments of FIG. 6, plane 308 represents an exemplary longitudinal location for the cross-sectional slice. Referring to block 504 of FIG. 4 and referring still to FIG. 6, the medical sensing system 100 identifies at least one revolution or frame (e.g., leading frame 602) ahead of the cross-sectional plane 308 in the longitudinal direction and at least one revolution or frame (e.g., lagging frame 604) behind the cross-sectional plane 308 in the longitudinal direction. In the procedure that follows, the medical sensing system 100 uses these two frames to interpolate imaging data that lies in the cross-sectional plane 308 rather than just flattening the acquired data.

Referring to block 506 of FIG. 5A and referring still to FIG. 6, the medical sensing system identifies a pixel 606 within the cross-sectional plane 308. The pixel 606 is a region of arbitrary size and may be identified by its cylindrical coordinates, a combination of the pixel's radial orientation (r), azimuthal orientation (θ), and longitudinal orientation (z). In the example of FIG. 6, the exemplary radial pixel 606 is selected, and the cylindrical coordinates (r, θ, z) are indicated. As explained below, imaging data values at the pixel 606 may be determined from acquired data values at corresponding radial and azimuthal orientations by compensating for the difference in longitudinal orientation.

Referring to block 508 of FIG. 5A and to FIGS. 6 and 7, the medical sensing system 100 acquires a signal intensity at a first point 608 in the first frame at a radial and azimuthal orientation that corresponds to the pixel 606 (e.g., the leading frame 602). The first point 608 may be beyond the imaging plane 308 and thus offset from the pixel in a longitudinal direction (e.g., leading or lagging). The signal intensity may correspond to ultrasound echo data, OCT data, and/or any other type of sensing data and may be in any representation including baseband, radio-frequency/time domain, and/or other suitable representation.

Referring to block 510 of FIG. 5A, the medical sensing system 100 determines the amount of longitudinal offset between the first point 608 and the pixel 606. In an exemplary embodiment with a known number of radial measurements per frame/revolution and a relatively constant pullback velocity, the longitudinal offset may be determined based on the number of radial measurements taken between the plane 308 of the pixel 606 and the first point 608. For example, if the plane 308 is known to coincide with radial measurement 0 and the first point 608 is acquired during radial measurement 128, the longitudinal offset may be determined by the difference of the two values. Accordingly, in such embodiments, the longitudinal offset may be expressed as a number of radial measurements, but may also be expressed as a distance value or time value. The longitudinal offset may be normalized so that the span of each frame is a fixed value, such as 1 or the number of radial measurements per frame.

Referring to block 512 of FIG. 5A and to FIG. 7, a weighting element 702 of the medical sensing system 100 determines a weighting factor for the first point 608 based on the longitudinal offset of block 510. The weighting factor reflects the certainty that a signal intensity at the pixel 606 corresponds to the signal intensity at the first point 608 and thus, is inversely proportional to the offset. In various embodiments, the weighting factor has a linear relationship and/or a higher-order polynomial relationship with the longitudinal offset. For example, the weighting factor may depend on the square of the longitudinal offset in order to place greater emphasis on values obtained near to the pixel 606.

Referring to block 514 of FIG. 5A and to FIGS. 6 and 7, the medical sensing system 100 acquires a signal intensity at a second point 610 in the second frame (e.g., lagging frame 604) at a radial and azimuthal orientation that corresponds to the pixel 606. The second point 610 may be beyond the imaging plane 308 and offset from the pixel 606 in the opposite longitudinal direction from the first point 608. Accordingly, the second point 610 may be the first point 608 delayed by a frame (or vice versa). The signal intensity may correspond to ultrasound echo data, OCT data, and/or any other type of sensing data and may be in any representation including baseband, radio-frequency/time domain, and/or other suitable representation. Referring to block 516 of FIG. 5A, the medical sensing system 100 determines the amount of longitudinal offset between the second point 610 and the pixel 606 substantially as described in block 510. Referring to block 518 of FIG. 5A and to FIG. 7, a second weighting element 702 of the medical sensing system 100 determines a second weighting factor to the second point 610 based on the determined offset of block 516. The second weighting factor reflects the certainty that a signal intensity at the pixel 606 corresponds to the signal intensity at the second point 610 and thus, is inversely proportional to the offset. In various embodiments, the second weighting factor has a linear relationship and/or a higher-order polynomial relationship with the longitudinal offset.

Referring to block 520 of FIG. 5B and to FIG. 7, an averaging element 704 of the medical sensing system 100 averages the weighted signal intensity at the first point 608 and the weighted signal intensity at the second point 610. This average signal intensity is an interpolated value and has at least some correlation to the signal intensity at the pixel 606. Accordingly, in some embodiments, the average signal intensity is used as the interpolated signal value at the pixel 606 without further processing. An image formed using average signal intensities may eliminate the seam found in other techniques and may reduce other distortion including curvature distortion.

However, the average signal intensity has a number of other artifacts, such as feature doubling, that can affect diagnosis. Feature doubling occurs when a strong reflective feature is located at a first position in a first frame and a second position in a second frame. The strong signal intensity dominates the weighted average so that the feature appears in both positions in the average. This may give the appearance of two separate and distinct features. Feature doubling may be caused by a stationary feature that extends along the longitudinal path but is somewhat skewed relative to the pullback path. It may also be caused by tissue moving faster than the frame rate and the under-sampling and the resultant aliasing. Furthermore, averaging is, in effect, a type of low pass filtering, and weak signal intensities are often obscured. As a result, the average signal intensity may exhibit resolution blurring and reduced sensitivity. These effects can complicate feature recognition, tissue characterization, tissue measurement, and other diagnostic efforts.

As an alternative, in some embodiments, the medical sensing system 100 uses the average signal intensity to determine a probability that the value at the pixel 606 closer to the signal intensity at the first point 608 than the second point 610 (or vice-versa). Referring to block 522 of FIG. 5B and to FIG. 7, a first comparator 706 of the medical sensing system 100 determines the difference between the average signal intensity and the signal intensity at the first point 608 to determine a first probability indicator. In some embodiments, the magnitudes (i.e., absolute values) of the average signal intensity and the signal intensity at the first point are compared and the probability indicator is expressed as a magnitude. Referring to block 524 of FIG. 5B and to FIG. 7, a second comparator 708 of the medical sensing system determines the difference between the average signal intensity and the signal intensity at the second point 610 to determine a second probability indicator. Here as well, in some embodiments, the magnitudes of the average signal intensity and the signal intensity at the second point are compared and the second probability indicator is expressed as a magnitude.

Referring to block 526 of FIG. 5B and to FIG. 7, a third comparator 710 of the medical sensing system 100 compares the first probability indicator to the second probability indicator, and the intensity at the pixel 606 is selected based on the comparison. In the embodiments of FIG. 7, a multiplexer selects the first signal intensity or the second signal intensity based on the result. In an example, the intensity at the first point 608 is selected to represent the intensity at the pixel 606 when the first probability indicator is greater, and the intensity at the second point 610 is selected to represent the intensity at the pixel 606 when the second probability indicator is greater. Referring to block 528, the selected signal intensity is provided for further signal processing, such as image filtering, envelope filtering, log compression, gamma curve adjustment, etc., in order to generate a diagnostic image. The processes of blocks 506-528 may be repeated for each pixel in the diagnostic image.

FIG. 8 is a representation of a de-seamed image 800 produced by the medical sensing system 100 according to embodiments of the present disclosure. As evident in FIG. 8, in many embodiments, the method 500 produces pixel intensities such that the resulting image does not have a seam. The resultant images may also depict vascular curvature more accurately. Furthermore, unlike average signal intensities, the pixel values selected by the method 500 do not exhibit feature doubling. Additionally, in many embodiments, the resultant image suffers no loss of resolution, blurring, or low-intensity filtering, which may occur from other seam-elimination techniques. As an additional benefit, the method 500 may be applied to any representation of the signal intensities and does not require prior conditioning to convert the data to a format such as baseband, radio-frequency (RF)/time domain, or any other representation.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A medical sensing system comprising:
a processing engine operable to receive a first signal at a first point corresponding to a pixel and a second signal at a second point corresponding to the pixel, wherein the processing engine includes:
an averaging element operable to determine a weighted average of the first signal and the second signal;
a first comparator operable to determine a first probability based on the first signal and the weighted average;
a second comparator operable to determine a second probability based on the second signal and the weighted average; and
a third comparator operable to:
select one of the first signal or the second signal as an imaging value of the pixel based on the first probability and the second probability; and
provide the selected imaging value of the pixel for forming an image.

2. The medical sensing system of claim 1, wherein the processing engine further comprises:
a first weighting element operable to determine a first weighting factor for the first point based on a longitudinal distance between the first point and the pixel; and
a second weighting element operable to determine a second weighting factor for the second point based on a longitudinal distance between the second point and the pixel, wherein the averaging element is further operable to further determine the weighted average based on the first weighting factor and the second weighting factor.

3. The medical sensing system of claim 2, wherein the first weighting element is further operable to determine the longitudinal distance between the first point and the pixel based on a count of radial measurements between the pixel and the first point, and wherein the second weighting element is further operable to determine the longitudinal distance between the second point and the pixel based on a count of radial measurements between the pixel and the second point.

4. The medical sensing system of claim 2, wherein the first weighting factor is inversely proportional to the longitudinal distance between the first point and the pixel, and wherein the second weighting factor is inversely proportional to the longitudinal distance between the second point and the pixel.

5. The medical sensing system of claim 1, wherein the processing engine is further operable to select the first point and the second point based on the first point and the second point each having a radial orientation and an azimuthal orientation corresponding to the pixel.

6. The medical sensing system of claim 1, wherein the first comparator is further operable to further determine the first probability based on a difference between the first signal and the weighted average, and wherein the second comparator is further operable to further determine the second probability based on a difference between the second signal and the weighted average.

7. The medical sensing system of claim 1, wherein the first comparator is further operable to further determine the first probability based on a difference between a magnitude of the first signal and a magnitude of the weighted average, and wherein the second comparator is further operable to further determine the second probability based on a difference between a magnitude of the second signal and the magnitude of the weighted average.

8. The medical sensing system of claim 1, wherein the first signal and the second signal represent one of: ultrasound echo data or optical coherence tomography data.

9. The medical sensing system of claim 1, wherein the first signal and the second signal are represented in one of: a baseband representation or a time-domain representation.

10. A method comprising:
receiving a first signal value associated with a first point located a first longitudinal distance from a pixel and a second signal value associated with a second point located a second longitudinal distance from the pixel;
determining a first probability associated with the first point based on the first longitudinal distance;
determining a second probability associated with the second point based on the second longitudinal distance;
selecting a signal value for the pixel based on the first probability and the second probability; and
providing the selected signal value for the pixel for forming an image.

11. The method of claim 10 further comprising:
determining a first weighting factor for the first point based on the first longitudinal distance;
determining a second weighting factor for the second point based on the second longitudinal distance;
determining a weighted average based on the first signal value, the first weighting factor, the second signal value, and the second weighting factor,
wherein the determining of the first probability includes comparing the first signal value to the weighted average, and
wherein the determining of the second probability includes comparing the second signal value to the weighted average.

12. The method of claim 11, wherein the first weighting factor is inversely proportional to the first longitudinal distance, and wherein the second weighting factor is inversely proportional to the second longitudinal distance.

13. The method of claim 10, wherein the selecting of the signal value for the pixel includes selecting the first signal value as the signal value for the pixel when the first probability is greater than the second probability.

14. The method of claim 10 further comprising:
determining the first longitudinal distance based on a count of radial measurements taken between the pixel and the first point; and
determining the second longitudinal distance based on a count of radial measurements taken between the pixel and the second point.

15. The method of claim 10, wherein each of the first point and the second point have a radial orientation and an azimuthal orientation corresponding to the pixel.

16. The method of claim 10 wherein the first signal value and the second signal value each represent one of: ultrasound echo data or optical coherence tomography data.

17. A method of diagnostic imaging, the method comprising:
identifying a pixel located between a first point and a second point in a longitudinal direction;
receiving a first imaging signal for the first point and a second imaging signal for the second point;
determining a weighted average of the first imaging signal and the second imaging signal;
comparing the first signal to the weighted average to determine a first probability;
comparing the second signal to the weighted average to determine a second probability;
selecting a value for the pixel based on the first probability and the second probability; and
providing the selected value for use in forming a diagnostic image.

18. The method of claim 17 further comprising:
determining a first weighting factor for the first imaging signal based on a longitudinal distance between the first point and the pixel;
determining a second weighting factor for the second imaging signal based on a longitudinal distance between the second point and the pixel,
wherein the determining of the weighted average includes applying the first weighting factor to the first imaging signal and applying the second weighting factor to the second imaging signal.

19. The method of claim 17, wherein the selecting of the value for the pixel includes selecting the first signal when the first probability is greater than the second probability.

20. The method of claim 17, wherein the first signal and the second signal are represented in one of: a baseband representation or a time-domain representation.

* * * * *